United States Patent [19]
Schlitzer et al.

[11] Patent Number: 5,462,713
[45] Date of Patent: Oct. 31, 1995

[54] DOUBLE REDOX SYSTEM FOR DISINFECTING CONTACT LENSES

[75] Inventors: Ronald L. Schlitzer, Fort Worth; N. L. Dassanayake; Rajkumar P. Bhatia, both of Arlington, all of Tex.

[73] Assignee: Alcon Laboratories, Inc., Fort Worth, Tex.

[21] Appl. No.: 107,268

[22] Filed: Aug. 16, 1993

Related U.S. Application Data

[62] Division of Ser. No. 928,643, Aug. 13, 1992, abandoned, which is a continuation of Ser. No. 526,759, May 22, 1990, abandoned.

[51] Int. Cl.$^6$ .......................... A01N 59/08; A01N 59/12; A61L 2/18
[52] U.S. Cl. .............................. 422/37; 422/30; 514/840; 424/661; 424/669
[58] Field of Search ................................. 422/37, 29, 34, 422/30; 252/105, 102, 95, 99, 106; 514/839, 840; 424/661, 665, 669–671

[56] References Cited

U.S. PATENT DOCUMENTS

| | | | |
|---|---|---|---|
| 3,120,378 | 2/1964 | Lee et al. | 252/95 |
| 3,136,716 | 6/1964 | Kitter | 504/133 |
| 3,248,281 | 4/1966 | Goodenough | 424/613 |
| 3,873,696 | 3/1975 | Randeri et al. | 424/680 |
| 3,911,107 | 10/1975 | Krezanoski | 422/37 X |
| 4,094,983 | 6/1978 | Bodor | 424/266 |
| 4,278,548 | 7/1981 | Bettinger et al. | 422/28 X |
| 4,312,833 | 1/1982 | Clough et al. | 422/30 |
| 4,588,586 | 5/1986 | Kessler et al. | 424/94 |
| 4,738,840 | 4/1988 | Simon et al. | 422/29 X |
| 4,767,559 | 8/1988 | Kruse et al. | 252/106 |
| 4,937,072 | 6/1990 | Kessler et al. | 424/94.4 |
| 4,971,765 | 11/1990 | Loretti et al. | 422/116 |
| 4,986,963 | 1/1991 | Corcoran et al. | 422/30 |
| 5,055,287 | 10/1991 | Kessler | 424/7.1 |
| 5,169,455 | 12/1992 | Kessler | 422/28 X |
| 5,213,760 | 5/1993 | Dziabo, Jr. et al. | 422/37 |

FOREIGN PATENT DOCUMENTS

| | | |
|---|---|---|
| 879564 | 8/1971 | Canada . |
| 0175801A1 | 4/1986 | European Pat. Off. . |
| 0196151 | 10/1986 | European Pat. Off. . |
| 1472410 | 5/1977 | United Kingdom . |
| 1604020 | 12/1981 | United Kingdom . |
| 89/00430 | 1/1989 | WIPO . |

OTHER PUBLICATIONS

Conn et al., "Iodine Disinfection of Hydrophilic Contact Lenses", *Annals of Ophthalmology*, pp. 361–364 (Mar. 1981).

Weast, Robert C., (ed.) *CRC Handbook of Chemical and Physics, 58th Ed.*, p. D-142.

Vogel, Arthur I., *A Text–Book of Quantitative Inorganic Analysis Including Elementary Instrument Analysis*, John Wiley & Sons, New York: 1961, p. 363.

*Primary Examiner*—Robert J. Warden
*Assistant Examiner*—E. Leigh Dawson
*Attorney, Agent, or Firm*—James A. Arno; Gregg C. Brown; Julie J. L. Cheng

[57] ABSTRACT

An improved method for rapid disinfection of contact lenses in a convenient and reliable manner is disclosed in which a series of oxidation-reduction reactions are employed. Specifically, dicheoroisocyanurate and potassium iodide react to form iodine species for disinfecting the contact lens. An amount of ascorbate is then added to neutralize the iodine species.

8 Claims, No Drawings

5,462,713

DOUBLE REDOX SYSTEM FOR DISINFECTING CONTACT LENSES

This is a divisional of U.S. patent application Ser. No. 07/928,643 filed on Aug. 13, 1992 now abandoned, which is a continuation of U.S. patent application Ser. No. 07/526,759 filed May 22, 1990.

BACKGROUND OF THE INVENTION

The present invention relates to an improved system for disinfecting human worn contact lenses. More particularly, this invention relates to a composition and method for disinfecting contact lenses wherein a sequence of oxidation-reduction reactions are employed to provide very potent and rapid disinfection capability.

Numerous systems for disinfecting contact lenses have been described in the prior art, including systems based on oxidation and reduction principles and systems based on the use of chlorine-containing compounds or iodine to disinfect. Reference is made to the following publications for further background regarding such systems:
European Patent Application 0 196 151 A2 (Hopkinson et al.);
U.S. Pat. No. 3,873,696 (Randeri et al.);
Canadian Patent No. 879,654 (Firth);
British Patent Specification 1 604 020 (Clough et al.);
U.S. Pat. No. 4,312,833 (Clough et al.); and
Conn et al., "Iodine Disinfection of Hydrophilic Contact Lenses," *Annals of Ophthalmology*, pages 361–364 (March 1981).

Many of these prior systems have had significant drawbacks such as inadequate disinfection, inconvenience, and discoloration of contact lenses. There has, therefore, been a continuing need for a disinfection system which is capable of achieving very rapid disinfection of contact lenses in a convenient and reliable manner. The present invention is directed to the provision of an improved system which satisfies this need.

SUMMARY OF THE INVENTION

The contact lens disinfection system of the present invention comprises two basic components: a first component which achieves disinfection of contact lenses and a second component which neutralizes the antimicrobial agents generated by the first component. For purposes of the present specification, the first component is referred to as the "disinfection component" and the second component is referred to as the "neutralization component."

The disinfection component comprises an unique combination of two types of antimicrobial agents, namely: an oxidizing agent, such as a peroxide or a hypohalite (such as sodium hypochlorite), and a reducing agent, such as an alkali metal salt of a halogen compound. The use of such oxidizing agents to disinfect contact lenses is well known, as is the use of halogen-containing compounds. However, the combined use of these agents is believed to be quite unique. The combination provides a system wherein the oxidizing agent is reduced, resulting in the generation of a product which is also a potent antimicrobial agent. The following equation illustrates this principle:

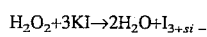

In this example, the hydrogen peroxide acts as an oxidizing agent having very potent antimicrobial activity, while the potassium iodide acts to reduce the hydrogen peroxide to water and iodine. As this reaction takes place, the initial disinfection achieved with the hydrogen peroxide is rapidly supplemented by the disinfection achieved with the iodine species produced by the reaction. Thus, the disinfection component of the present invention entails the use of two very potent disinfecting agents. This allows contact lenses to be disinfected extremely rapidly and effectively.

The neutralization component of the present invention is a reducing agent which acts to neutralize the product of the reaction between the oxidizing and reducing agents of the disinfection component, as further illustrated by the following equation:

The neutralization component may comprise any organic or inorganic compound capable of reducing residual halogen resulting from the reaction of the oxidizing and reducing agents of the disinfection component.

The above-described contact lens disinfection system has numerous advantages over prior systems. For example, the disinfection component has very potent antimicrobial activity and, as a result, the system is capable of disinfecting contact lenses in less than ten minutes, which is much more rapid than most prior disinfection methods. The system is also much more convenient to use than prior disinfection methods because it simply requires the addition of one or two tablets to a solution containing contaminated lenses. Further, in a preferred embodiment, the system is self-preserved, due to the antimicrobial activity of the neutralization component. This feature ensures that the disinfected contact lenses will not become recontaminated during storage subsequent to being disinfected with the disinfection component.

DETAILED DESCRIPTION OF THE INVENTION

The oxidizing agents which may be utilized in the present invention include: peracids, peroxides, N-haloorganic compounds and their alkali metal salts, chlorites, chlorine dioxide, and hypohalites. Suitable peroxides include: hydrogen peroxide, peroxyacids, peroxyesters, alkylperoxides, acylperoxides, succinic acid peroxide, organic hydroperoxidates (e.g., urea peroxide or mannitol peroxide), and inorganic hydroperoxidates (e.g., alkali metal salts of perborates, percarbonates, persulfates and perphosphates). The preferred oxidizing agents are: hydrogen peroxide, the inorganic hydroperoxidates cited above, particularly sodium percarbonate and sodium perborate, and hypochlorite-generating compounds, particularly N-chloroorganic compounds such as dichloroisocyanurate.

The reducing agents which may be utilized in conjunction with the above-described oxidizing agents to form the disinfection component of the present invention include the interhalogen compounds, which are those halogen compounds where two different halogen atoms are combined, such as iodine monochloride. The reducing agents also include organic halides such as N-iodo succinimide and alkali metal salts of halogen compounds such as potassium iodide or potassium bromide which are capable of: (1) reducing oxidizing agents such as hypochlorites and peroxides and (2) producing halogen species having antimicrobial activity. The preferred reducing agent is potassium iodide.

The above-described oxidizing and reducing agents are utilized in amounts effective to eliminate substantially or to reduce significantly the number of viable microorganisms present on contact lenses subsequent to treatment of the lenses with aqueous solutions containing a combination of these agents, in accordance with the established requirements of the United States Food and Drug Administration and analogous governmental authorities in other countries. For purposes of the present specification, that amount is referred to as an "antimicrobial effective amount." As will be appreciated by those skilled in the art, the amount of each agent utilized may vary depending on factors such as the particular combination of agents selected, the type of lens care regimen in which the present system is utilized (e.g., whether a daily cleaner is used and the effectiveness of such a cleaner), and the type of lens being treated (e.g., "hard" versus "soft"). In general, the disinfection component of the present invention will comprise one or more oxidizing agents in an amount sufficient to provide a concentration of about 0.00001 percent by weight/volume (w/v %) to about 1.0 w/v % and one or more reducing agents in an amount sufficient to provide a concentration of about 0.001 w/v % to about 1.0 w/v %. The minimum amount of reducing agent required will primarily be determined by the amount of oxidizing agent utilized.

The neutralization component of the present invention may be any compound capable of reducing the halogen species produced by the disinfection component, including: ascorbic acid and its salts and isomers, alkyl-substituted and unsubstituted sulphur-containing amino acids, sulfites, bisulfites, dihydroxy maleic acid, alkyl-substituted (e.g., 5-methyl reductic acid) and unsubstituted reductic acid, thioglycollate, and thiosulfate. The preferred reducing agents for use as the neutralization component of the present invention are ascorbates, particularly sodium ascorbate. The neutralization component will be utilized in an amount effective to neutralize any halogen species generated as the result of the reaction between the oxidizing and reducing agents of the disinfection component. More than the stoichiometric amount is needed to provide a reducing solution since these are equilibrium reactions. The amount of reducing agent required in order to accomplish this objective will typically be an amount sufficient to provide a concentration of about 0.001 w/v % to about 1.0 w/v %. In a preferred embodiment, a 20 millimole excess of sodium ascorbate is used as the neutralization component.

The components of the present contact lens disinfection system may be formulated in various forms, in accordance with techniques known by those skilled in the art. For example, the disinfection and neutralization components can be incorporated into a single tablet which is composed in a manner such that the neutralization component is released after the lenses have been disinfected by the disinfection component. Separate tablets, solutions, or any combination thereof, can also be utilized, so long as the neutralization component is released into the system after a slight time delay, in order to allow the disinfection component to work.

Release of the ingredients of the neutralization component into the saline solution or other suitable diluent acts to neutralize the disinfection component and must therefore be delayed. This is accomplished either by physically delaying addition of the neutralization component to the diluent, or by utilizing a seal coating and/or a delayed release coating to slow or delay dissolution of the neutralization component.

As will be appreciated by those skilled in the art, the seal and delayed release coatings may comprise various types of materials. For example, the seal coating may be composed of any of several polymeric materials, including cellulose ethers, vinyls, glycols, and acrylics, or the coating could be composed of synthetic or natural gums, gelatin, shellac, salts (e.g., sodium chloride), saccharide alcohols (e.g., mannitol or sorbitol), or other commonly used seal coating materials. The delayed release coating can be composed of any of several polymeric materials, including cellulose ethers, vinyls, glycols, and acrylics. The delayed release coating may additionally include plasticizers such as propylene glycol, polyethylene glycol, glycerin, mineral oil, vegetable oil, or other known plasticizers.

In a preferred embodiment of the present invention, the disinfection component comprises a combination of sodium dichloroisocyanurate as the oxidizing agent and potassium iodide as the reducing agent, and the neutralization component comprises sodium ascorbate. When these agents are combined in an aqueous solution, the reaction scheme is as follows:

1) dichloroisocyanurate+$H_2O$→cyanuric acid+HOCl
2) HOCl+KI→HOI+$Cl^-$
   HOI+$I^-$→$I_2$
   $I_2$+$I^-$→$I_3^-$
3) $I_3^-$+Ascorbate→Iodide+Dehydroascorbate In a typical use of the present invention, the lens to be disinfected is cleaned with an approved daily cleaner and added to a specified volume of saline solution or other suitable diluent (e.g., distilled water) in a suitable container. If hydrogen peroxide is utilized as the oxidizing agent, then the hydrogen peroxide solution can be utilized as the diluent. The tablet(s) of the present invention can be added to the diluent either immediately before or immediately after addition of the lens. As the tablet(s) dissolve, the oxidizing and reducing agents of the disinfection component are released into the solution and the lenses are disinfected. Release of the ingredients of the neutralization component into the solution acts to neutralize the products of the reaction between the oxidizing and reducing agents and must therefore be delayed. This is accomplished either by physically delaying addition of the neutralization component, or by providing the neutralization component with a delayed release coating, as described above, in which case the neutralization and disinfection components can be added to the diluent at the same time.

The following examples are presented to illustrate further the disinfection system of the present invention, but are not intended to limit the scope of the invention in any respect.

EXAMPLE 1

The following formulation represents an embodiment of the invention wherein the oxidizing agent portion of the disinfection component is contained in one tablet and all other portions of the system, including the reducing agent portion of the disinfection component, are contained in a separate tablet.

| | mg/Tablet |
|---|---|
| Part I — Oxidizing Agent | |
| Ingredient | |
| Sodium Dichloroisocyanurate | 0.065 |
| Sodium Carbonate (anhydrous) | 12.70 |

|                                  | mg/Tablet       |
|----------------------------------|-----------------|
| Sodium Bicarbonate               | 13.435          |
| Adipic Acid                      | 23.80           |
| Part II — Reducing Agent/Neutralizing Core | |
| A. Neutralizing Core             |                 |
| Sodium Ascorbate                 | 5.0 + 10% excess |
| Sodium Bicarbonate               | 8.5             |
| Citric Acid (anhydrous)          | 3.5             |
| Polyethylene Glycol 3,350 Powder | 4.0             |
| Lactose                          | 23.5            |
| B. Seal Coating                  |                 |
| Hydroxy Methyl Cellulose         | 1.125           |
| Ethanol (USP, Dehydrated)        | 0.017 ml        |
| Purified Water                   | 4.27            |
| C. Delayed Release Coating       |                 |
| Acrylic Acid Ester (30% solids w/w) | 3.13         |
| Polyethylene Glycol (8,000)      | 0.35            |
| Purified Water                   | 24.07           |
| D. Outer Layer                   |                 |
| Potassium Iodide                 | 2.0 + 10% excess |
| Sodium Chloride                  | 0.94            |
| Hydroxypropyl Methyl Cellulose (2910, E-5 premium) | 0.157 |
| Purified Water                   | 18.74           |

Preparation

In preparing the tablet containing the oxidizing agent, the sodium dichloroisocyanurate and adipic acid were each passed through a suitable screen (e.g., 200 micron mesh) or granulator prior to mixing with the sodium carbonate and sodium bicarbonate in a V-shell blender for one hour. The resultant granulation was compressed using a suitable tooling and tablet press to obtain slugs. The slugs were then broken and once more mixed in a V-shell blender for one hour. The granulation was then compressed using a rotary tablet press fitted with suitable tooling into tablets weighing approximately 50 mg and having a hardness of 5 to 10 Strong-Cobb units.

The ingredients of the neutralizing core were combined and formed into tablets in a similar manner. These tablets were then sequentially coated with a seal coating and a delayed release coating, followed by an outer coating of potassium iodide. Each of the three coating solutions was similarly prepared by mixing the ingredients until a homogenous mixture was obtained. Each of the coating solutions was applied by rotating the tablets and spraying the coating solution onto the tablet.

All portions of tablet preparation should be done under low humidity conditions (below 20% relative humidity).

EXAMPLE 2

The following formulation represents an embodiment of this invention wherein the oxidizing agent and reducing agent portions of the disinfection component and the neutralization component are formulated into three separate tablets.

|                                  | mg/Tablet |
|----------------------------------|-----------|
| Part I — Disinfection Component  |           |
| A. Reducing Agent                |           |
| Boric Acid                       | 20.0      |
| Mannitol                         | 35.0      |
| Potassium Iodide                 | 20.0      |
| Sodium Bicarbonate               | 20.0      |
| Adipic Acid                      | 15.0      |
| B. Oxidizing Agent               |           |
| Boric Acid                       | 25.0      |
| Mannitol                         | 40.0      |
| Sodium Bicarbonate               | 22.0      |
| Sodium Percarbonate              | 11.0      |
| Adipic Acid                      | 12.0      |
| Part II — Neutralization Component |         |
| Ingredient                       |           |
| Sodium Ascorbate                 | 40.0      |
| Sodium Bicarbonate               | 10.5      |
| Citric Acid                      | 4.5       |
| Polyethylene Glycol 3,350        | 5.0       |
| Lactose DT                       | 43.0      |
| Sodium Borate                    | 22.0      |

Preparation

The tablets may be prepared in a manner similar to the procedure described in Example 1, above. The same ingredients could also be formulated as a single tablet having three layers, wherein the core is composed of Part II and the outer layers are composed of the oxidizing and reducing agents of Part I.

EXAMPLE 3

The disinfecting effectiveness of the system of the present invention was evaluated by determining the rate and extent of kill for a six logarithm challenge inocula. Ten milliliters (ml) of sterile isotonic saline solution were inoculated with a standardized suspension of *Aspergillus fumigatus* (ATCC 10894), *Candida albicans* (ATCC 10231), *Pseudomonas aeruginosa* (ATCC 15442), *Serratia marcescens* (ATCC 14041), and *Staphylococcus aureus* (ATCC 6538) to obtain a final concentration of at least one million microorganisms per milliliter. The two tablets of Example 1 were added to the saline suspension. At selected times, 1 ml was withdrawn, serially diluted in Dey/Engley neutralizing broth, and pour plates prepared. Petri plates and dilution tubes were incubated and the number of survivors recovered were quantitated.

The results demonstrated that the test system had both bactericidal and fungicidal activity. No survivors of bacteria or yeast were recovered after five minutes exposure. After ten minutes exposure, *A. fumigatus*, the most resistant microorganism tested, was reduced by at least six logarithms, depending on the actual microorganism concentration. The following Table shows the results of a typical experiment where the antimicrobial activity of the system of the present invention was compared with that of 3% hydrogen peroxide against *A. fumigatus*.

TABLE 1

| Relative Survivors of *Aspergillus fumigatus* | | |
|---|---|---|
| Exposure Time | Double Redox | 3% $H_2O_2$ |
| Initial | $1.9 \times 10^6$ | $1.9 \times 10^6$ |

TABLE 1-continued

Relative Survivors of *Aspergillus fumigatus*

| Exposure Time | Double Redox | 3% $H_2O_2$ |
|---|---|---|
| 10 min | $2.0 \times 10^1$ | $8.5 \times 10^5$ |
| 20 min | $1.5 \times 10^1$ | $6.0 \times 10^5$ |

The overall efficacy of the system of the present invention for disinfecting contact lenses was also determined. Ten soft contact lenses belonging to FDA Lens Group IV were contaminated with one million spores of *A. fumigatus* suspended in serum and dead yeast cells. Each lens was cleaned with a daily lens cleaner and rinsed with nonpreserved saline. Lenses were placed in a basket-type contact lens case. Nonpreserved saline was added to the lens case up to the fill line (10 ml). The two tablets described in Example 1 were placed in the lens case and the lid with the lenses screwed onto the case. After 20 minutes, each lens was rinsed with unpreserved saline and placed in 100 ml Dey/Engley broth. The 10 ml of neutralized solution in each lens case was decanted into 100 ml Dey/Engley broth. Each lens case was filled with agar containing neutralizers and the lid with baskets replaced. After two weeks incubation, the Dey/Engley broths and lens cases were observed for surviving *A. fumigatus*. No *A. fumigatus* was recovered from any of the ten lenses, their solutions, or the lens cases.

The effectiveness of the neutralization component of this system to inhibit the growth of microorganisms that may inadvertently be introduced into the lens case subsequent to the lens disinfection process was established by means of a series of similar experiments. In these experiments 10 ml of unpreserved saline were placed into separate sterile test tubes. The two tablets described in Example 1 were added and allowed to dissolve. After dissolution the solution in each test tube was challenged with bacteria and fungi such that after adding the microorganisms, the test solution contained at least 100,000 Colony Formation Units per ml (CFU/ml). At selected times, 1 ml was withdrawn from each tube, serially diluted in Dey/Engley broth, pour plates prepared and survivors determined as previously described. Results of a typical experiment of this type are given in Table 2, below.

TABLE 2

Inhibition of Microorganisms by the Neutralization Component

| Microorganism | Colony Formation Units/ml | | | | |
|---|---|---|---|---|---|
| | Initial | 1 Day | 2 Days | 7 Days | 14 Days |
| *Aspergillus niger* | $9.1 \times 10^4$ | $2.3 \times 10^4$ | $5.8 \times 10^3$ | $3.3 \times 10^3$ | $3.9 \times 10^2$ |
| *Aspergillus fumigatus* | $1.1 \times 10^5$ | $7.3 \times 10^4$ | $6.5 \times 10^4$ | $4.7 \times 10^4$ | $6.8 \times 10^3$ |
| *Candida albicans* | $9.0 \times 10^4$ | $9.8 \times 10^4$ | $6.0 \times 10^4$ | $1.4 \times 10^4$ | $1.0 \times 10^3$ |
| *Escherichia coli* | $1.1 \times 10^5$ | $7.8 \times 10^4$ | $6.9 \times 10^4$ | $1.4 \times 10^6$ | $5.3 \times 10^4$ |
| *Pseudomonas aeruginosa* | $8.9 \times 10^4$ | $2.8 \times 10^4$ | $1.3 \times 10^3$ | <10 | <10 |
| *Serratia marcescens* | $1.5 \times 10^5$ | $1.7 \times 10^5$ | $1.2 \times 10^5$ | $5.2 \times 10^3$ | $1.8 \times 10^3$ |
| *Staphylococcus aureus* | $1.5 \times 10^5$ | $1.9 \times 10^4$ | $2.2 \times 10^2$ | <10 | <10 |
| *Staphylococcus epidermidis* | $6.9 \times 10^4$ | $1.9 \times 10^4$ | $1.4 \times 10^3$ | <10 | <10 |

The neutralization component was effective in inhibiting the proliferation of bacteria, yeast and molds and maintaining the concentration of viable microorganisms below the initial challenge concentration.

The invention in its broader aspects is not limited to the specific details shown and described above. Departures may be made from such details within the scope of the accompanying claims without departing from the principles of the invention and without sacrificing its advantages.

We claim:

1. An improved method for rapidly and effectively disinfecting a contact lens, comprising:
   (a) providing a contact lens to be disinfected;
   (b) placing the lens in an aqueous solution;
   (c) providing a water soluble salt of dichloroisocyanurate as a source of hypochlorite and providing a source of a water soluble iodide salt;
   (d) forming a disinfecting solution by releasing an antimicrobial effective amount of hypochlorite and iodide in said aqueous solution, said hypochlorite and iodide reacting to form halogen species including iodine species, whereby the lens is rapidly and effectively disinfected by the combined actions of the hypochlorite and the halogen species;
   (e) providing a source of ascorbate; and
   (f) releasing an amount of ascorbate in said disinfecting solution sufficient to neutralize said iodine species.

2. A method according to claim 1, wherein the concentration of hypochlorite in the disinfecting solution is 0.00001 to 1.0 w/v % and the concentration of potassium iodide in the disinfecting solution is 0.001 to 1.0 w/v %.

3. A method according to claim 1, wherein the ascorbate preserves the disinfecting solution against microbial contamination following disinfection of the lens.

4. A method according to claim 1, wherein the lens is disinfected in less than ten minutes.

5. A method according to claim 1, wherein the dichloroisocyanurate salt is contained in a first tablet and is released in the aqueous solution by dissolving said first tablet in the aqueous solution, and the iodide salt and ascorbate are contained in a second tablet and are sequentially released in the aqueous solution by dissolving the second tablet in the aqueous solution, so that the dichloroisocyanurate salt and iodide salt can react to form iodine species and disinfect the lens prior to release of the ascorbate.

6. A method according to claim 5, wherein the second tablet includes means for delaying the release of the ascorbate relative to the release of the iodide salt.

7. A method according to claim 6, wherein the second tablet includes an inner core containing the ascorbate, a delayed release coating surrounding the core, and an outer layer containing the iodide salt.

8. A method according to claim 1, wherein the water soluble salt of dichloroisocyanurate is a sodium salt and the water soluble iodide salt is a potassium salt.

* * * * *